United States Patent [19]

Notarianni et al.

[11] Patent Number: 5,103,212

[45] Date of Patent: Apr. 7, 1992

[54] BALANCED FLUID FLOW DELIVERY SYSTEM

[75] Inventors: Kathy A. Notarianni, North Bethesda, Md.; Joseph A. Senecal, Wellesley, Mass.

[73] Assignee: Worcester Polytechnic Institute, Worcester, Mass.

[21] Appl. No.: 375,251

[22] Filed: Jul. 3, 1989

[51] Int. Cl.$^5$ .............................................. G08B 17/10
[52] U.S. Cl. .................................. 340/628; 73/863.01
[58] Field of Search ...................... 340/627, 628, 693; 73/863.33, 863.01, 863.02, 863.03; 356/37

[56] References Cited

U.S. PATENT DOCUMENTS

| | | | |
|---|---|---|---|
| 3,678,487 | 7/1972 | Ludewig, Jr. et al. | 340/628 |
| 3,777,571 | 12/1973 | Jaeger | 73/863.81 |
| 3,960,500 | 6/1976 | Ross et al. | 73/863.11 |
| 4,051,753 | 10/1977 | Bohl et al. | 73/863.33 |
| 4,090,392 | 5/1978 | Smith et al. | 13/863.33 |
| 4,194,191 | 3/1980 | Salem | 340/515 |
| 4,254,414 | 3/1981 | Street et al. | 340/627 |
| 4,293,217 | 10/1981 | Bird, Jr. et al. | 356/37 |
| 4,532,814 | 8/1985 | Lalin | 73/863.03 |
| 4,608,556 | 8/1986 | Cole | 340/628 |
| 4,764,758 | 8/1988 | Skala | 340/627 |

FOREIGN PATENT DOCUMENTS

| | | | |
|---|---|---|---|
| 0290412 | 11/1988 | European Pat. Off. | 340/628 |
| 2846310 | 4/1980 | Fed. Rep. of Germany | 340/693 |

OTHER PUBLICATIONS

Installation Manual for Early Warning Smoke Detection Apparatus (VESDS) by Fenwal Incorporated of Ashland.

Thesis of Co-Inventor, K. Notarianni, dated Aug. 1988, Describing the Various Aspects of the Invention.

Primary Examiner—Jin F. Ng
Assistant Examiner—Jill Jackson
Attorney, Agent, or Firm—Hamilton, Brook, Smith & Reynolds

[57] ABSTRACT

A multi-port system sampling maintains a balanced fluid flow, and more particularly is a gas sampling system used for the rapid detection of fire in which the flow rate through each sampling system aperture is substantially equal. The system may include a single main conduit having a number of sampling apertures spaced apart for sampling different locations. The sizing of the apertures is such that an equal flow rate is present at each aperture, allowing a balanced sampling of each sampling location. The system may also include multiple secondary conduits all feeding one main conduit. Each secondary conduit has a number of different sampling apertures, and may be of a different length. The diameters of the secondary conduits are relative to the length of the conduits and the size of the respective conduit apertures so as to create a balanced fluid flow rate through each of the apertures.

11 Claims, 4 Drawing Sheets

BALANCED FLUID FLOW DELIVERY SYSTEM

BACKGROUND

There is a continuing need to improve on systems for detecting a fire in its early stages. In particular, today's high technology companies have created a growing number of operational environments within which a significant loss can result from even a small fire. Other areas, such as group homes and hotels, where extensive egress time is necessary due to lack of mobility of the occupants or unfamiliarity of the occupants with their surroundings, can make the speed of fire detection a question of life or death.

To date, the fastest detectors employ continuous sampling type detection systems which use a sampling tube network to draw air samples from an area to be protected into the detection device. By using these networked sampling tubes, a single detector may replace a number of point type detectors. However, because the sampling tube networks carry air samples from a number of different locations to the sensor, it is imperative that networks be designed to obtain predictable performance.

The two primary performance characteristics of a smoke detection system are sensitivity and response time. In a continuous sampling type smoke detection system, the sensor threshold is the smoke density which must enter the sensor unit to cause actuation of the detector. However, this is not equal to the smoke density which must enter a sampling orifice in the sampling network since the smoke sample is diluted while entering a sampling orifice by clean air entering other orifices outside the smoky area. The smoke density sampled at an orifice must therefore be greater than the threshold of the sensor in order to provide a sufficient density at the detector to cause actuation. The smoke density which must be present in the protected area to cause actuation of the sensor, taking into account these dilution effects, is termed the alarm threshold, and defines the sensitivity of the sampling orifice.

The response time of each sampling orifice is defined as the time it takes an air sample entering a sampling orifice to travel to the sensor. In a multi-orifice sampling tube, the response time from each sampling orifice decreases along the sampling tube in the direction of the sensor due to 1) the shorter distance of travel and 2) the increase in air flow rate in the system as each sampling orifice is passed.

Both the sensitivity and response time of each sampling orifice are dependent upon the rate of sampling at that orifice. When equal sized orifices are placed along the sampling tube, the rate of sampling decreases along the sampling tube in the direction away from the sensor, due to the loss of suction pressure in the sampling tube caused by friction. Equal diameter sampling orifices, therefore, do not sample at equal rates and overall performance of the system is unbalanced. Because the system is unbalanced, air enters different sampling orifices at different rates, and therefore smoke entering different orifices undergo unequal dilution effects. Thus, different smoke concentrations in different protected zones are required to achieve an alarm threshold at the sensor.

SUMMARY OF THE INVENTION

A fire detection system is provided which detects combustion in one or more monitored zones. The system has a detector which detects a threshold concentration of particulate matter such as is characteristically given off during various stages of combustion. The detector has a detection chamber into which fluid samples are drawn. The detector may be a submicrometer particle counting detector, a light scattering type photoelectric detector, or a condensation nuclei type detector. A fluid pump, or any suitable device for driving the fluid, is in fluid communication with the detection chamber such that fluid samples are drawn into the detection chamber. Also in fluid communication with the detection chamber is a sampling tube through which fluid samples are drawn. Operation of the pump causes fluid to flow through the sampling tube and into the detection chamber. The sampling tube has a plurality of orifices or apertures through which fluid samples are drawn from the monitored zones into the sampling tube. The orifices are individually sized to provide a fluid intake rate which is substantially equal at each orifice. By "substantially equal" it is signified that the flow rate through each aperture within a 10% margin, and preferably, less than 5%.

Also provided with the present invention is a multi-branch sampling network having a main tubing of a predetermined diameter. The main tubing has a first and a second end, with a constant flow rate provided by a pump in fluid communication with the first end for drawing a constant flow through the tubing. A plurality of branch tubings, each having a first and a second end, are arranged such that the first end of each branch of tubing is in fluid communication with the second end of the main tubing. The length of each branch of tubing is provided with apertures opened to a different gaseous region to be sampled. The diameters of the individual branch tubes relative to one another in this embodiment are chosen to provide the desired response time at each aperture.

A method of fabricating the balanced fire detection system of the above-referenced embodiments of the invention can also be employed in the manufacturing of a variety of balanced fluid flow delivery systems suitable for many different applications. Any system in which it is desirable to deliver a predetermined amount of fluid through a fixed multiport system can employ the present method and the resulting apparatus.

The systems' design constraints including the number of apertures, the total length of the duct system or tubing, and the distance from each aperture to the detector or fluid source can be used to determine the size of each aperture to deliver the desired amount of fluid either, into or out of, each aperture. A software module can be developed for each particular application which is used in standard data processing systems to produce the necessary specifications for that application.

The above, and other features of the invention including various novel details of construction and combination of parts, will now be more particularly described with reference to the accompanying drawings and pointed out in the claims. It will be understood that the particular balanced fluid flow delivery system embodying the invention is shown by way of illustration only and not as a limitation of the invention. The principal features of this invention may be employed in various embodiments without departing from the scope of the invention.

DETAILED DESCRIPTION OF THE PREFERRED EMBODIMENTS

Figure 1:
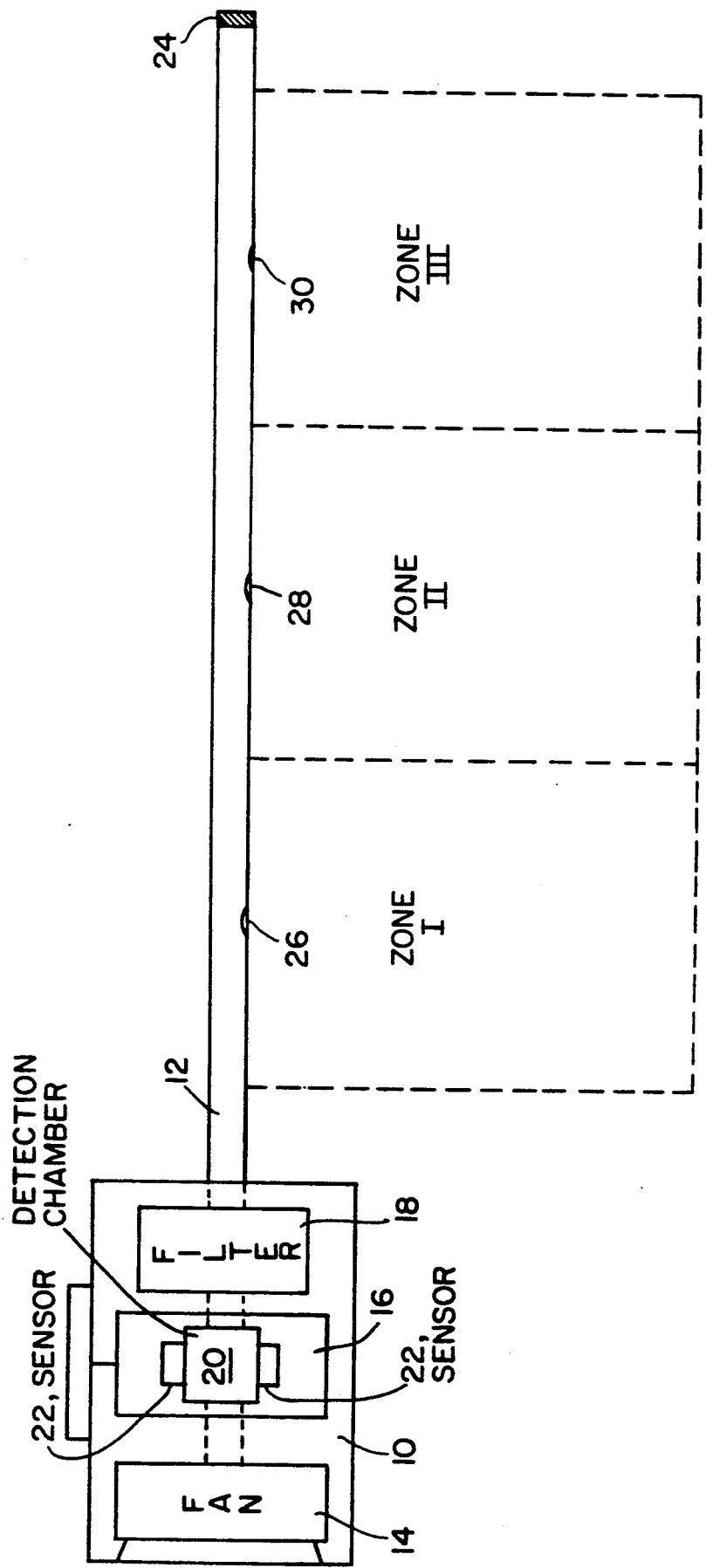
FIG. 1 shows a schematic view of a fire detection system of the present invention using a single sampling tube with multiple orifices.

A preferred embodiment of a fire detection system is illustrated in FIG. 1. The system has a detector assembly 10 which is connected to and in fluid communication with a multiple orifice sampling tube 12. A fluid connection links the sampling tube 12 to a detector 16 within the detector assembly 10 through a filter 18. The detector, in turn, is in fluid communication with a fan 14 which when operated generates an air flow through the detector assembly drawing air samples into the apertures 26, 28, 30 of sampling tube 12. From the tube 12 the samples are drawn through filter 18 and into a detection chamber 20 of the detector 16.

The detector 16 is a submicrometer particle counting detector and uses photosensors 22 to detect a threshold concentration of such particles. Since an abundance of submicrometer particles are given off in the earliest stages of combustion, the detector is adjusted to provide a fast response. However, the detector 16 may also be a photoelectric type detector, a condensation nuclei detector, or one of the other detector types commonly known in the art. The fan 14 continuously draws samples into the detector chamber 20 from regions to be monitored, making the detection system a "continuous sampling" system. This system allows fast response time for the detector and therefore very quick detection of a fire in the regions from which air samples are drawn.

As shown in FIG. 1, the sampling tube 12 is sealed at the end 24 which is positioned adjacent the last aperture. The sampling tube draws its air samples through the apertures, or orifices, 26, 28, 30 disposed along the length of the tube 12. Since the apertures of the FIG. 1 tubing are formed directly into the tubing, the size of each variable is pre-determined and non-adjustable. Each orifice 26, 28, 30 draws air samples from a different region to be protected from fire. As shown, orifice 26 draws air from zone 1, orifice 28 draws from zone 2, and orifice 30 draws from zone 3. The dotted lines of FIG. 1 are for illustrative purposes only and do not necessarily define boundaries between air space. The designations for zones 1, 2 and 3 show how a single multi-orifice sampling tube 12 can monitor a number of different sampling regions. The orifices 26, 28 and 30 can sample air from different enclosed regions, or alternatively can just take air samples from different parts of a large room. The sampling tube 12 is custom designed for the application with the number of orifices being selected by the number of regions which need protecting. The sampling tube 12 can be as long as 250 feet, for example, depending on the strength of the fan 14 the sensitivity of the detector 16, and the number of orifices in the tube 12.

In order to achieve the same fire detection performance for each zone monitored by the detection system 10, the intake flow from the orifices 26, 28 and 30 is balanced such that the volumetric flow rate of air through each sampling orifice is equal.

The volumetric air flow rate in the sampling tube increases towards the sensor as air is admitted to the sampling tube through the sampling orifices. The volumetric flow rate of air through a sampling orifice is described by the orifice equation:

$$Q_{o,i} = C/\rho(A_{o,i})(2g_c(P_{amb} - P_i)\rho)^{\frac{1}{2}}$$

where:

$Q_{o,i}$ = volumetric flow rate of air through sampling orifice i, ft$^3$/s
C = orifice coefficient, experimentally determined
$A_{o,i}$ = cross-sectional area of sampling orifice i, ft$^2$
$g_c$ = gravitational constant
$P_{amb}$ = ambient atmospheric pressure, lb/ft$^2$ and,
$\rho$ = density of air, lb/ft$^3$ The orifice equation assumes steady, fully-developed laminar, incompressible flow. For each sampling orifice i, the internal suction pressure $P_{s,i}$, varies due to friction losses along the sampling tube. Therefore, to achieve equal sampling from all sampling orifices, the cross-sectional area $A_{o,i}$ of the sampling orifice must be varied accordingly to achieve an equal volumetric flow rate at each orifice. Since the rate of air intake through a sampling orifice is proportional to the square root of the suction pressure inside the sampling tube at the point where an orifice i opens into the tube, the diameter of orifice i is inversely proportional to the square root of $P_i$. The volumetric flow rate of air in the sampling tube system at any given orifice i, can be described by a mass balance:

$$A_s(V_{s,i}) = A_s(V_{s,i-1}) + A_o(V_{o,i-1})$$

wherein $A_o * V_{o,i}$ is the volumetric flow rate through orifice i. Because the flow is balanced, this quantity is the same for all sampling orifices. The volumetric flow rate through each orifice is directly equal to the total system flow rate (the flow rate through the detector) divided by the total number of sampling orifices.

Suction pressure in the system is a maximum at the fan and decreases along the sampling tube towards the most remote end of the sampling tube. Losses in suction pressure are due to friction caused by the flow of air through the system. A higher flow rate of air causes increased friction and thus a greater loss of suction pressure.

The pressure drop in a single, straight length of sampling tube can be expressed by the Hagen-Poiseuille equation. The Hagen-Poiseuille equation assumes steady, fully-developed, laminar, incompressible flow and can be expressed:

$$\Delta P = (32 \Delta L (V_{s,i}) \mu)/(D_s^2)(g_c)$$

where $\Delta L$ = length of the sampling tube (ft)
$V_{s,i}$ = velocity of the fluid in the sampling tube at aperture s; and
$D_s$ = diameter of the sampling tube or from standard dynamics charts for turbulent flow. Depending on the Reynolds # in that section of pipe.

Using the above expression provides a method by which to determine the suction pressure at a single orifice located some distance along a straight sampling tube. However, if there are any bends in the sampling tube used to turn the flow, loss of suction pressure through these bends will be higher than through the straight portion of the tube. The bends in the sampling tube are most often provided by elbow joints. Elbow joints provide a 90° turn in the flow direction, and the two most common types of elbow joints are the "standard" elbow joint and the "sweep" elbow joint. The sweep elbow joint has a larger radius bend than the standard elbow, and thereby has a lower pressure loss than the standard elbow.

In order to account for the bends in the sampling tube in the suction pressure equation, the losses due to the elbows are expressed in terms of an equivalent length of straight pipe. These equivalents, experimentally determined, are labelled $\Delta P_{std}$, for the standard elbow, and $\Delta P_{swp}$, for the sweep elbow.

To determine the suction pressure at the aperture closest to the control unit, the following pressure equation is used:

$$P_1 = P_{fan} + \Delta P_{det/filt} + \Delta P_{o1} + N_{std}(\Delta P_{std}) + N_{swp}(\Delta P_{swp})$$

where:
$P_{fan}$ = fan suction pressure (negative)
$\Delta P_{det/fil}$ = pressure loss due for the detector and filter (experimentally determined)
$\Delta P_{o1}$ = straight tube pressure loss from the detector to the first orifice
$N_{std}$ = number of standard elbows between the detector and the first orifice
$N_{swp}$ = number of sweep elbows between the detector and the first orifice Once the suction pressure at the first orifice is determined, the pressure at the remaining orifices in the sampling tube can also be determined. To determine the pressure of a subsequent orifice, the loss in suction pressure between the orifice in question and the previous orifice must be determined. This pressure loss can be expressed as:

$$P_{i-(i+1)} = \Delta P_{ST(i-(i+1))} + N_{std}(P_{std}) + N_{swp}(P_{swp})$$

where $P_{i-(i+1)}$ is the total loss of suction pressure between sampling orifices i and i+1, and $P_{ST(i-(i+1))}$ is the pressure loss through the length of straight tubing between sampling orifices i and i+1. $N_{std}(P_{std})$ and $N_{swp}(P_{swp})$ again refer to the number of standard and sweep elbows between the two orifices, respectively.

The volumetric air flow rate in the sampling tube increases towards the sensor as air is admitted to the sampling tube through the sampling orifices. To account for the changing flow velocity in the sampling tube, a momentum balance equation is generated using Bernoulli's equation.

$$P_{i+1} + (\tfrac{1}{2}g_c(\alpha_{i+1})(V_{i+1})\rho_{i+1}) = P_i + (\tfrac{1}{2}g_c\alpha_i \cdot V_i\rho_i) - P_{i-(i+1)}$$

The volumetric air flow rate and internal suction pressure can thus be calculated at all sampling orifices along the sampling tube network. Once the internal suction pressure profile along the sampling tube is known, the orifice diameters necessary to achieve equal intake of air at all sampling orifices are calculated by use of the previously discussed orifice equation. The orifice equation expressed in terms of orifice diameter is:

$$D_i = ((4Q_i)\rho/(C\pi(2\rho g_c(P_{amb}-P_i))^{\tfrac{1}{2}}))^{\tfrac{1}{2}}$$

$Q_i$, the volumetric flow rate through each orifice is equal to the volumetric flow rate through the detector divided by the total number of sampling orifices.

Balanced flow methodology, as presented above, thus allows for a continuous sampling smoke detector to be customized to a particular fire protection situation. This method provides a means by which a hydraulically balanced system can be fabricated in a non-empirical manner. It can also be used to determine sensitivity and response time of continuous sampling type detectors.

Response time, $t_{resp}$, is defined as the time it takes smoke entering a sampling orifice to travel to the detector. Response times are calculated from each sampling orifice by summing the lengths of sampling tube between sampling orifices and dividing by the velocity of air in that section of sampling tube.

$$t_{resp} = \Sigma L_i / V_i$$

Because of the dilution effect of clean air entering some of the sampling orifices, the sensitivity, or alarm threshold, of a sampling orifice is not equal to the sensitivity of the detector. With balanced sampling, the dilution effect of each sampling orifice taking in clean air is the same since all the orifices have the same intake flow rate. Maximum dilution is experienced when only one orifice is sampling smoke while all the others are drawing in clean air. This often happens when a multi-orifice sampling tube network is used to protect a multi-room or multi-compartmented area with one orifice assigned to each compartment or room. In such a case, the smoke entering a sampling orifice is diluted by a factor equal to the total number of sampling orifices in the system. Therefore, the concentration of smoke entering a single sampling orifice must be equal to the sensitivity of the detector times the number of sampling orifices in order to be sufficient enough to cause actuation of the detector.

The smoke concentration at a sampling orifice necessary to actuate the detector is referred to as the effective sensitivity, or alarm threshold, of the sampling orifice. The effective sensitivity of a single sampling orifice refers to a worst case dilution where only one sampling orifice samples clean air. It is expressed by:

$$C_{smoke} = (N)(sensitivity\ of\ the\ detector)$$

where $C_{smoke}$ is the concentration of smoke (% obscuration/ft) necessary at orifice i when the sensor threshold is reached and N is the total number of sampling orifices in the system.

Figure 2:
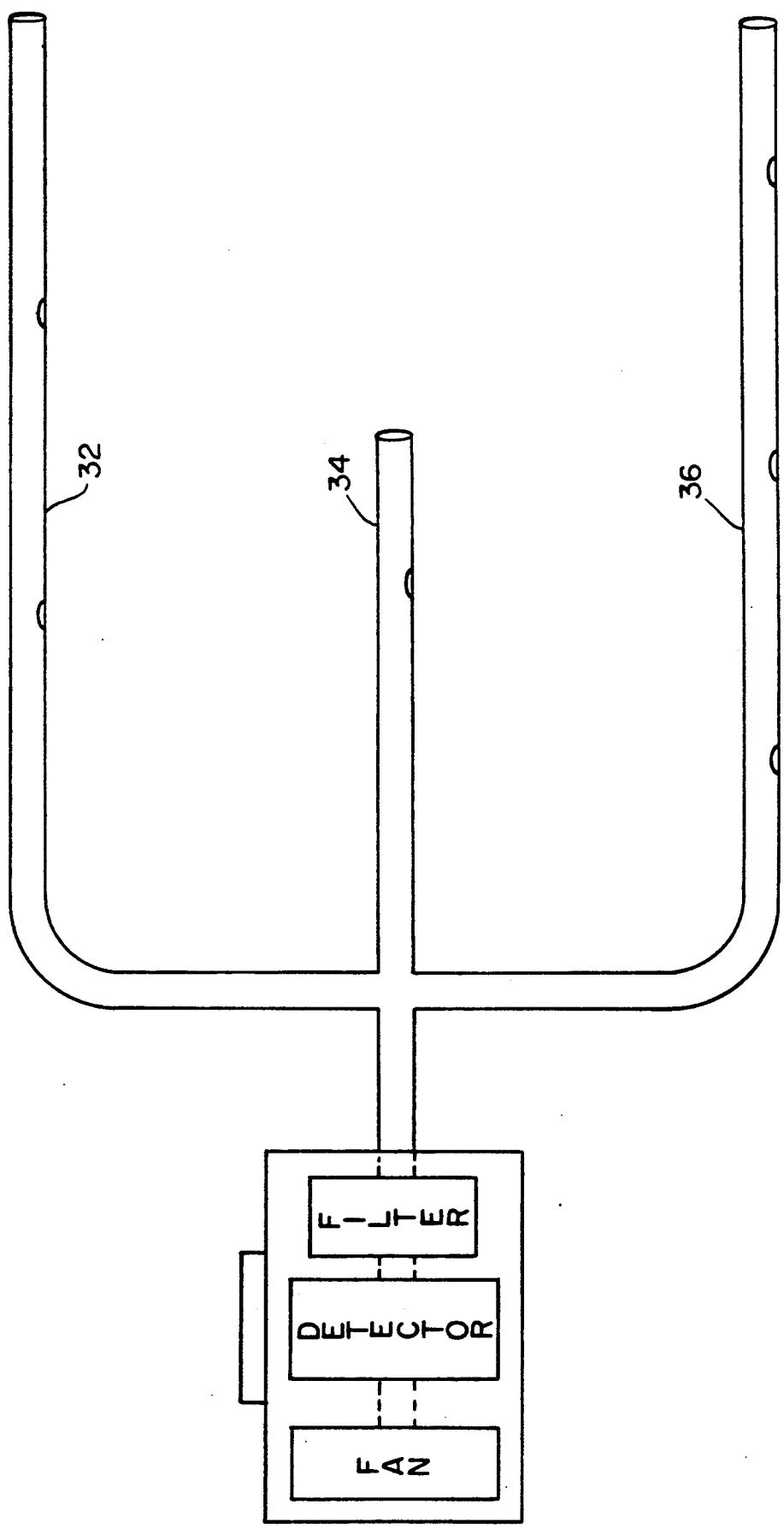
FIG. 2 shows a schematic view of a fire detection system a multi-branch sampling network, the branches having multiple orifices.

Referring to FIG. 2, the detector assembly is connected to a multi-branch sampling network. The system is customized and samples air from different locations. Each branch of the network has the same diameter, but is of a different length and has a different number of orifices. However, since for a balanced system each orifice must have the same volumetric flow rate, the previously developed balanced flow methodology is easily applied. The total number of apertures in the system of FIG. 2 is six. Branch 32 has one, branch 34 has two, and branch 36 has three. By knowing the overall flow rate through the detector assembly, the flow rate through each branch is easily determined. Branch 32 has one sixth of the overall flow, branch 34 has one third of the overall flow, and branch 36 has one half of the overall flow. Each branch of the network is thereby isolated and can be analyzed for orifice size using the balanced flow method as applied to the single sampling tube embodiment.

Figure 3:
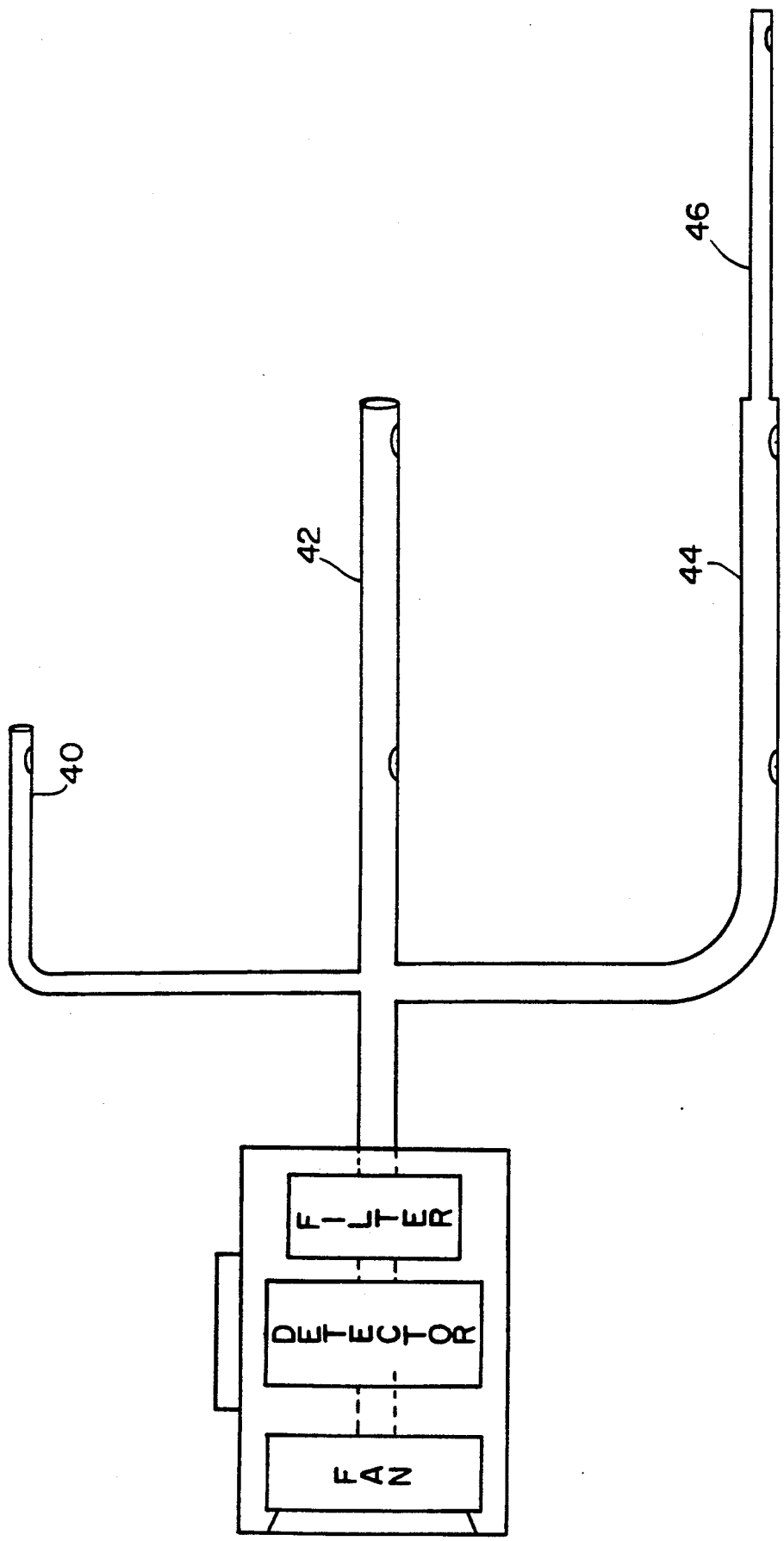
FIG. 3 shows a schematic view of a fire detection system having a multi-branch sampling tube network where different branches, or portions of branches have differing diameters.

In FIG. 3 another preferred embodiment of the invention is illustrated in which there are three different branches 40, 42 and 44 where the entire branch 40 has a different diameter than the other branches. Also, the end portion 46 of branch 44 has a smaller diameter. Note that the aperture and pipe sections can be provided using standard polyvinylchloride fittings that are commonly used in industry. Thus there is no need for specialized fittings to construct the present system.

Figure 4:
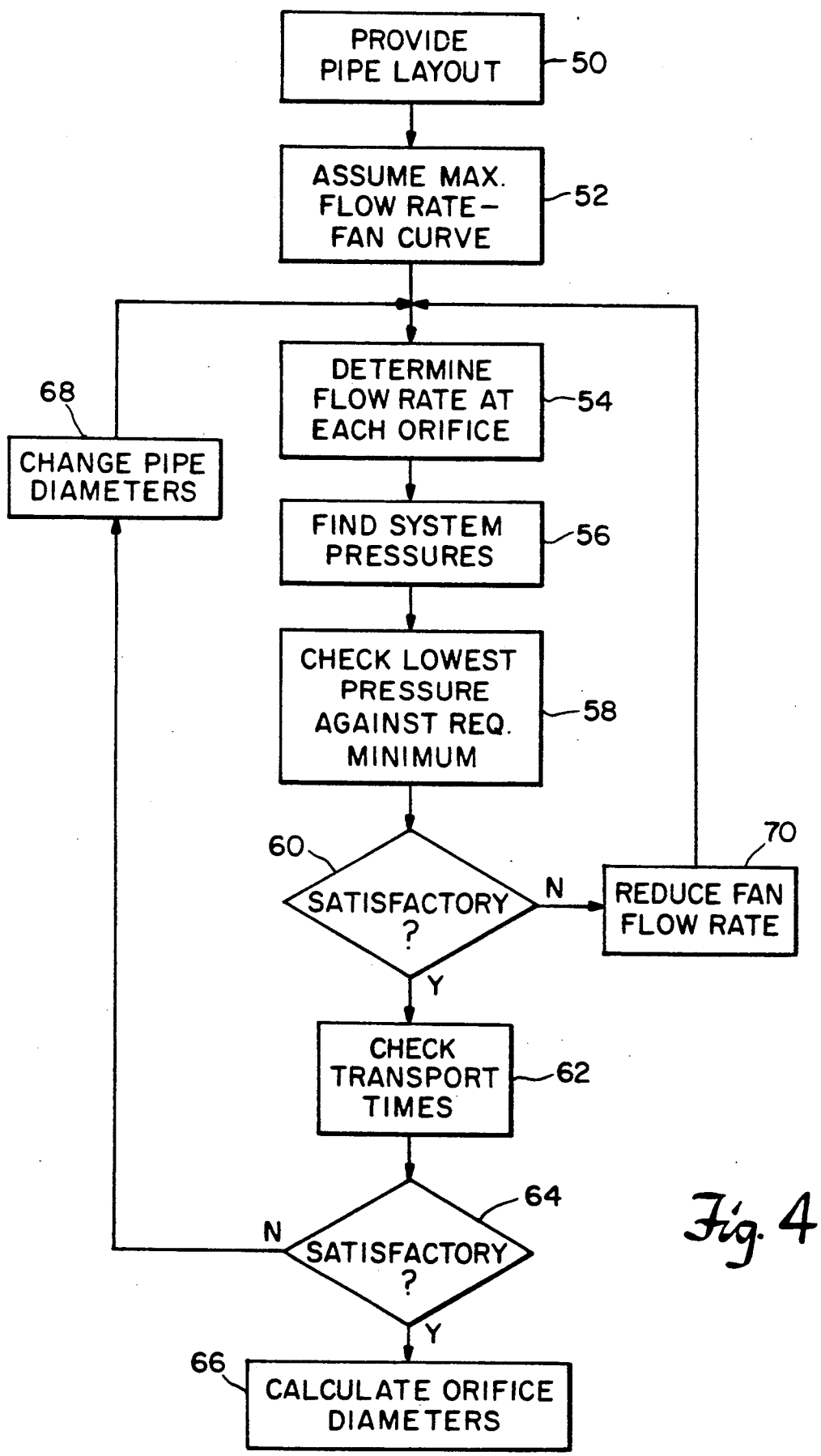
FIG. 4 is a process flow diagram of a method for fabrication a sampling tube network of the present invention.

The process flow diagram of FIG. 4 outlines a method of fabricating a sampling tube network as provided for in the present invention. This fabrication process can be performed in large part on any suitable data processing system. The pipe layout must be provided 50, including locations of all sampling orifices. The procedure begins with an assumption of the flow rate pulled by the fluid driver to be equal to its maximum value 52. This is obtained from the fan curve, suction pressure vs. flow rate. The flow rate through each orifice is then determined from the flowrate pulled by the driver divided by the total number of orifices in the network. By summing flow rates, the flow in the sampling tube at each point is then known 54.

The suction pressure available at each orifice is calculated by subtracting all pressure losses from the fluid driver to that orifice 56. The lowest suction pressure in the system is checked against a required minimum pressure 58/60. If the minimum required suction pressure cannot be met, 70, steps 54 through 60 are repeated. When pressure requirements have been met, transport time, defined as the time it takes a sample from the intake at the furthest orifice from the detector to travel to the detector is then checked against system requirements 62.

If transport time is satisfactory 64, orifice diameters required for balanced sampling are calculated, 66. If transport time is not satisfactory, tube diameters are changed to larger or smaller values according to where in the system the pressure losses per foot of tubing are greatest or least respectively 68. The calculation procedure then returns to step 54 redetermine the suction pressures and flow rates in the system and ensure that the lowest suction pressure is still within minimum requirements.

We claim:

1. In a continuous sampling fire detection system having a fluid drive, a detector, and a sampling tube network requiring a known number of orifices in known locations in the network, a method of fabricating the network such that the system is hydraulically balanced, the method comprising:

providing a suction pressure versus flow rate performance relation for the fluid drive;
assuming a maximum fluid drive flow rate for the system and determining a corresponding fluid drive suction pressure from the flow rate performance relation;
providing a suction pressure loss versus flow rate through system components;
assuming a consistent value for tube diameter throughout the sampling tube network;
assuming the flow rate through each orifice to be the maximum fluid drive flow rate divided by the number of orifices in the system;
determining the pressure losses in the straight lengths of sampling tube using the assumed flow velocities, the assumed tube diameter, and the tube lengths;
determining the point of lowest suction pressure in the system and calculating the assumed pressure at that point in the system using the assumed orifice flow rates and the provided pressure loss values;
comparing the assumed lowest pressure of the system to the required minimum system pressure and decreasing the assumed flow rate of the fluid drive until the system assumed lowest suction pressure meets minimum requirements;
determining the new fluid drive flow rate corresponding to the new assumed fluid drive suction pressure;
redetermining the assumed orifice flow rates and system pressure losses using the new fluid drive flow rate and suction pressure;
determining the diameter of each orifice in the sampling tube network by substituting the new system flow rates and suction pressures into the orifice equation for air;
boring the orifices in the tubes of the sampling tube network and assembling the system.

2. The method of claim 1 further comprising:
determining the largest response time in the system, after achieving a suction pressure minimum standards;
comparing the determined response time with minimum system requirements:
adjusting the diameter of selected sections of sampling tube redetermining the flow rates and suction pressures through the system still assuring a suction pressure within minimum requirements until the required response times are achieved.

3. The method of claim 1, further comprising performing selected steps of the method of fabrication on a data processor.

4. In a sampling fire detection system having a fluid drive, a detector, and a sampling tube with a known number of apertures, a method of fabricating the sampling tube comprising:

selecting a fluid drive flow rate for the system and determining a corresponding fluid drive suction pressure;
determining an aperture flow rate equal to the fluid drive flow rate divided by the total number of apertures in the sampling tube;
determining sampling tube pressures along the length of the sampling tube as a function of the aperture flow rate and the locations of the apertures along the length of the tube;
selecting a minimum sampling tube pressure and comparing it to the lowest of the determined sampling tube pressures;
modifying the selected fluid drive flow rate to establish new sampling tube pressures the lowest of which is substantially equal to the selected minimum sampling tube pressure;
determining a new aperture flow rate which corresponds to the modified fluid drive flow rate;
determining the diameter of each aperture as a function of the new aperture flow rate and the new sampling tube pressures; and forming the apertures in the sampling tube network according to the determined diameters.

5. A method according to claim 4 wherein the step of determining sample tube pressures further comprises determining pressure drops due to elbow joints along the length of the tube.

6. A method according to claim 5 wherein the step of determining sample tube pressures comprises determining the suction pressure of a first aperture closest to the fluid drive as a function of the fluid drive pressure and an air friction loss between the fluid drive and the first aperture.

7. A method according to claim 6 wherein the step of determining sample tube pressures further comprises determining the pressure loss between apertures as a function of the air friction loss attributable to the distance between apertures.

8. In a sampling fire detection system having a fluid drive, a detector and a multi-branch sampling network having a plurality of sampling tubes each with a known number of apertures, a method of fabricating the sampling network comprising:

selecting a fluid drive flow rate for the system and determining a corresponding fluid drive suction pressure;

determining the flow rate through each sampling tube of the sampling network as a function of the fluid drive pressure and the number of apertures in each tube;

determining an aperture flow rate for the apertures of each sampling tube, the aperture flow rate for an aperture being equal to the flow rate through the sampling tube in which said aperture is located divided by the number of apertures in that tube;

determining sampling tube pressures along the length of each sampling tube as a function of the aperture flow rates and the locations of the apertures along the length of the tubes;

selecting a minimum sampling tube pressure and comparing it to the lowest of the determined sampling tube pressures;

modifying the selected fluid drive flow rate to establish new sampling tube pressures the lowest of which is substantially equal to the selected minimum sampling tube pressure;

determining new aperture flow rates for each sampling tube which correspond to the modified fluid drive flow rate;

determining the diameter of each aperture as a function of the new aperture flow rates and the new sampling tube pressures; and forming the apertures in the sampling tube network according to the determined diameters.

9. A method according to claim 8 further comprising selecting the diameters of the sampling tubes of the network to improve the equalization of the flow rates through the tubes of the network.

10. A method of fabricating a gas sampling network comprising:

providing a data processor;

providing data inputs to the data processor to designate input parameters of a desired network, the parameters including a number of sampling points, locations of sampling points relative to a location of a fluid drive, and size and shape of tubing to be used in realizing the sampling network;

processing the data inputs with the data processor to provide output data indicative of the varied sizes of individual apertures to be placed in said tubing each at one of the sampling points, the size of the apertures being such that the fluid flow rate through each aperture is substantially equal; and forming apertures of varied sizes in the tubing according to the output data provided.

11. A method according to claim 10 further comprising providing a detector coupled to the tubing to detect particles given off during combustion.

* * * * *